(12) United States Patent
Ziltz et al.

(10) Patent No.: US 10,520,448 B2
(45) Date of Patent: Dec. 31, 2019

(54) METHOD AND SYSTEM FOR DETECTING ABNORMALITIES IN COATED SUBSTRATES

(71) Applicant: Grey Gecko LLC, Newport News, VA (US)

(72) Inventors: Austin Ziltz, Williamsburg, VA (US); Keith Reed, Newport News, VA (US)

(73) Assignee: Grey Gecko LLC, Newport News, VA (US)

( * ) Notice: Subject to any disclaimer, the term of this patent is extended or adjusted under 35 U.S.C. 154(b) by 0 days.

(21) Appl. No.: 16/420,120

(22) Filed: May 22, 2019

(65) Prior Publication Data

US 2019/0360941 A1    Nov. 28, 2019

Related U.S. Application Data

(63) Continuation-in-part of application No. 15/986,660, filed on May 22, 2018.

(51) Int. Cl.

| | |
|---|---|
| *G01N 21/88* | (2006.01) |
| *H04N 5/21* | (2006.01) |
| *H04N 7/18* | (2006.01) |
| *G01N 21/84* | (2006.01) |
| *H04N 5/225* | (2006.01) |

(52) U.S. Cl.
CPC ......... *G01N 21/8806* (2013.01); *H04N 5/211* (2013.01); *H04N 5/2252* (2013.01); *H04N 5/2256* (2013.01); *H04N 7/183* (2013.01); *G01N 2021/8427* (2013.01); *G01N 2021/8835* (2013.01)

(58) Field of Classification Search
CPC ....... G01N 21/8806; G01N 2021/8835; G01N 2021/8427; H04N 5/2256; H04N 5/2252; H04N 7/183; H04N 5/211
USPC ......................................................... 348/128
See application file for complete search history.

(56) References Cited

U.S. PATENT DOCUMENTS

| | | | |
|---|---|---|---|
| 2016/0142610 A1* | 5/2016 | Rivard | H04N 5/2356 |
| 2016/0195726 A1* | 7/2016 | Fujishiro | G02B 27/0176 345/8 |
| 2017/0150070 A1* | 5/2017 | Johansson | H04N 5/33 |
| 2017/0336328 A1* | 11/2017 | Gupta | G01N 21/8422 |

* cited by examiner

*Primary Examiner* — Jared Walker
(74) *Attorney, Agent, or Firm* — McAuley and Associates; Deidre McAuley

(57) ABSTRACT

Provided is a detection system for detecting abnormalities in a coated substrate having a coating and a substrate, and including a detection device that includes a housing configured to block external sources of light from impinging on the coated substrate, a light source array including a plurality of light sources and configured to be arranged to direct light upon the coated substrate, an optical imaging system configured to capture a video data stream and still images of the coating and an underlying surface of the substrate including structure features comprising any abnormalities in the coated substrate, an on-board embedded system to control the light source array and the optical imaging system and perform real-time processing to correct spatial and temporal variations in intensity of the plurality of light sources of the light source array, and spatial and temporal variations in sensitivity and optical Narcissus effect of the optical imaging system.

18 Claims, 5 Drawing Sheets

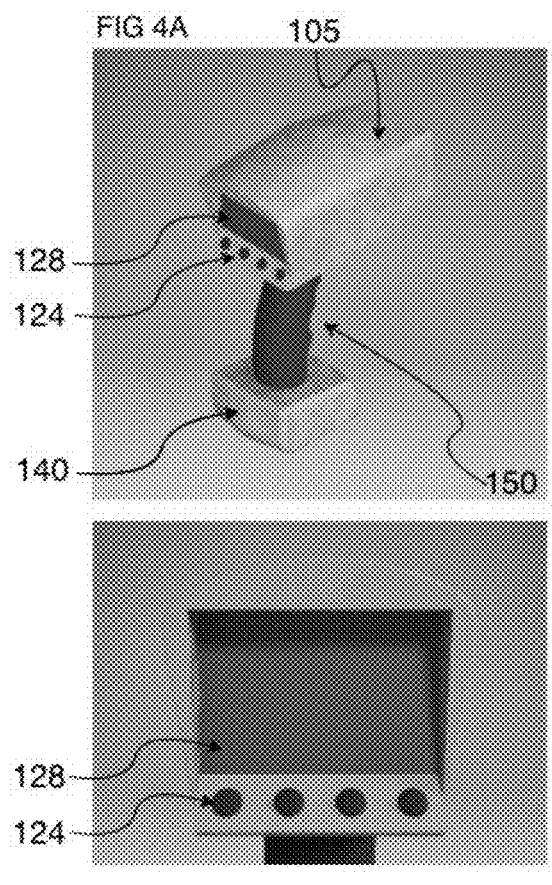
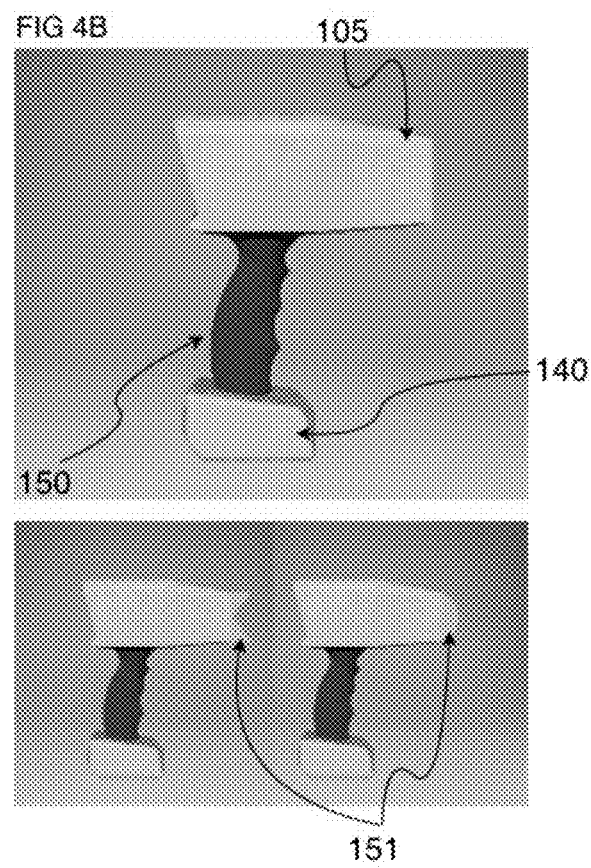
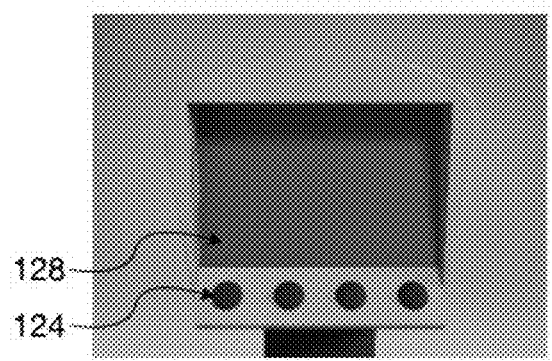
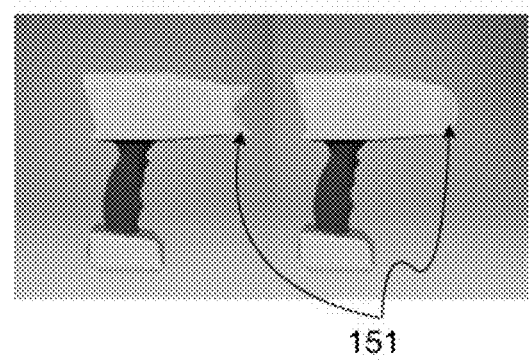

METHOD AND SYSTEM FOR DETECTING ABNORMALITIES IN COATED SUBSTRATES

I. CROSS REFERENCE

This application is a non-provisional, continuation-in-part application claiming priority to Non-Provisional application Ser. No. 15/986,660 filed on May 22, 2018, which claims priority to Provisional Application Ser. No. 62/509,621 filed on May 22, 2017, the contents of which is incorporated herein in its entirety

II. TECHNICAL FIELD

The present invention relates generally to a method detecting abnormalities in coated substrates. More particularly, the present invention relates to a method and system for detecting abnormalities on the surfaces directly below the coating.

III. BACKGROUND

Structures such as buildings, automobiles, marine vehicles and aircrafts are typically coated for preventative and aesthetic purposes and experience degradation based on environmental conditions. The environmental conditions can include rain, high winds, humidity, heat and salt spray, and other conditions which can potentially cause external and internal damages to the substrates of the structures. Some problems detected include corrosion, mold, cracks, scratches, delamination, and material fatigue, for example.

Conventional methods of detecting these abnormalities include visual inspection, x-ray, eddy current and capacitance point measurements or heating the substrate to generate infrared light for detection of any abnormalities of the substrate.

IV. SUMMARY OF THE EMBODIMENTS

Given the aforementioned deficiencies, a detection system for detecting abnormalities in underlying surface of a coated substrate that includes a housing having interchangeable forebodies (noses) formed to block external sources of light from impinging on the coated substrate in numerous different application geometries; a light source array of a plurality of light sources configurable to be (i) intensity modulated, (ii) matched in bandwidth to a spectral transmission band of the coating, and (iii) arranged to direct light upon the coated substrate; an optical imaging system matched to a wavelength range of the light source array and positioned to collect and measure reflected and scattered light from the coated substrate and generate an image of structural features including any abnormalities in the coated substrate; and an on-board embedded system configured to perform real-time image processing to correct spatial and temporal variations in the intensity of the light source array intensity and sensitivity of the optical imaging system, thereby improving fidelity of the measurement operation performed, as well as negating the use of a tablet PC or other peripheral allowing single-hand operation.

According to one or more embodiments, a detection software module is accessed via the on-board embedded system in communication with the optical imaging system.

Further, according to one or more embodiments a wearable head-up display (HUD) is in communication with the on-board embedded system to remotely view output and status of the detection system to allow single-hand operation of the measurement.

The communication performed within the detection system and within the on-board embedded system can be performed via wireless communication or wired communication.

According to yet another embodiment a detection method implemented by the above-identified system is provided.

The foregoing has broadly outlined some of the aspects and features of various embodiments, which should be construed to be merely illustrative of various potential applications of the disclosure. Other beneficial results can be obtained by applying the disclosed information in a different manner or by combining various aspects of the disclosed embodiments. Accordingly, other aspects and a more comprehensive understanding may be obtained by referring to the detailed description of the exemplary embodiments taken in conjunction with the accompanying drawings, in addition to the scope defined by the claims.

V. DESCRIPTION OF THE DRAWINGS

FIGS. 4A, 4B, 4C and 4D illustrates various applications of the detection system according to one or more embodiments.

Figure 1:
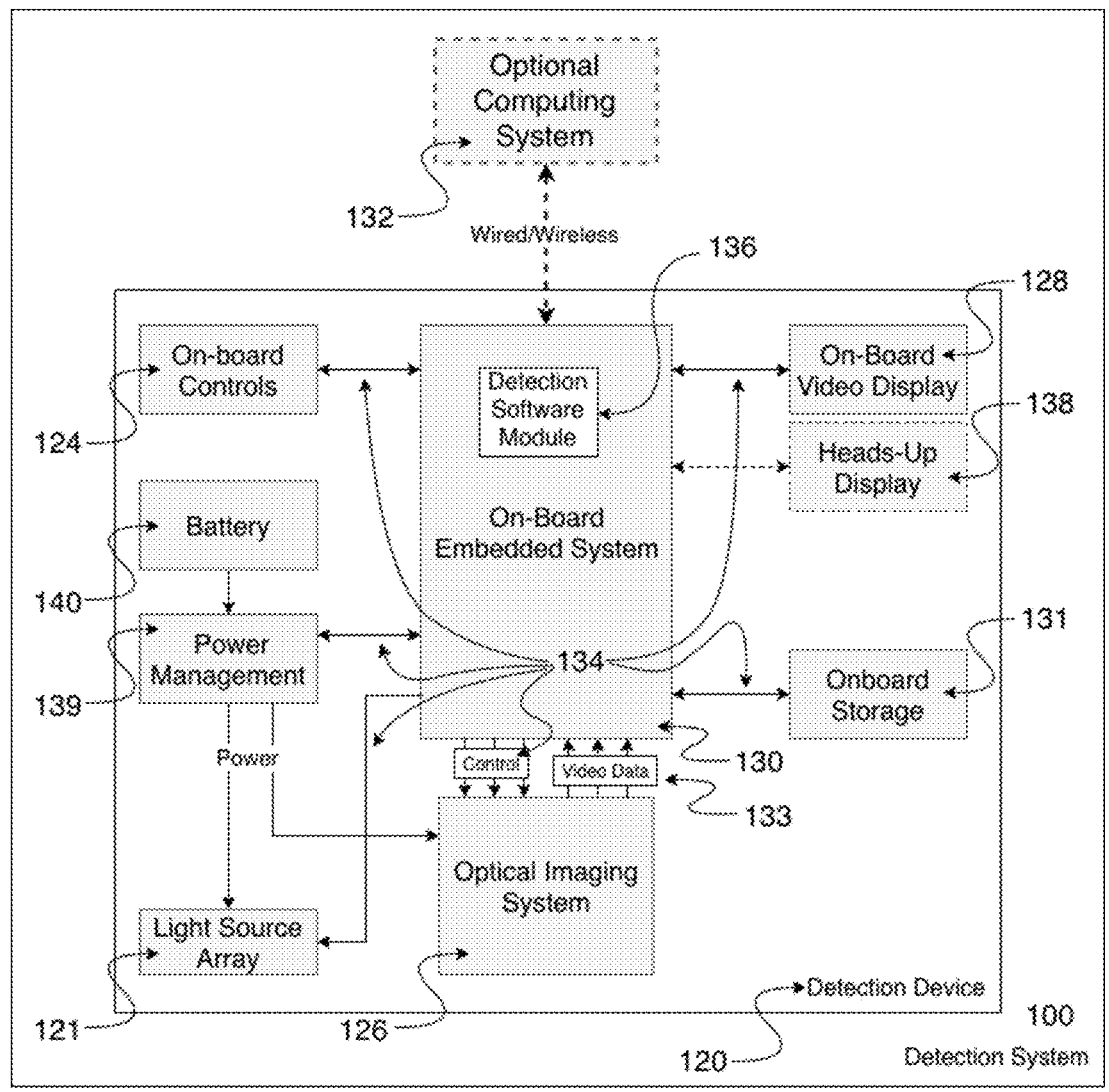
FIG. 1 is a block diagram illustrating the detection system according to one or more embodiments.

The drawings are only for purposes of illustrating preferred embodiments and are not to be construed as limiting the disclosure. Given the following enabling description of the drawings, the novel aspects of the present disclosure should become evident to a person of ordinary skill in the art. This detailed description uses numerical and letter designations to refer to features in the drawings. Like or similar designations in the drawings and description have been used to refer to like or similar parts of embodiments of the invention.

VI. DETAILED DESCRIPTION OF THE EMBODIMENTS

As required, detailed embodiments are disclosed herein. It must be understood that the disclosed embodiments are merely exemplary of various and alternative forms. As used herein, the word "exemplary" is used expansively to refer to embodiments that serve as illustrations, specimens, models, or patterns. The figures are not necessarily to scale and some features may be exaggerated or minimized to show details of particular components.

In other instances, well-known components, systems, materials, or methods that are known to those having ordinary skill in the art have not been described in detail in order to avoid obscuring the present disclosure. Therefore, specific structural and functional details disclosed herein are not to be interpreted as limiting, but merely as a basis for the claims and as a representative basis for teaching one skilled in the art.

As noted above, embodiments of the present invention include a detection system and a detection method thereof, including an optical imaging system and light source array to capture video data stream of an underlying surface of a coated substrate in order to detect any abnormalities such as corrosion, cracks, scratches, delamination, and material fatigue. The system is capable of detecting damage before it has compromised structural integrity of the underlying substrate or its coating. The detection system is also capable of identifying hidden fasteners, structural features such as welds, seams, joints, grounding connections and lightning arrestors, reading obscured/embedded codes or part numbers (e.g., serial numbers), inspecting composite substrates for damage, revealing previously repairs substrates, identifying weakened/thinned regions of coatings on substrates which need to be replaced/repaired and performing quality assurance inspections of recently applied coatings and repairs.

FIG. 1 is a block diagram illustrating the detection system 100 according to one or more embodiments. The detection system 100 includes a detection device 100 comprising a light source array 121 having a plurality of light sources 122, onboard controls 124 and an optical imaging system 126 in communication with an on-board embedded system 130.

The onboard controls 124 provide functions such as on/off function of the optical imaging system 126, the light source array 121 and an onboard video display 128 having touch-screen capabilities. In addition, the onboard controls 124 are configured to perform an operation of obtaining still images from the video data stream 133 (e.g., a digital video data stream). The onboard controls 124 connect to the on-board embedded system 130 to adjust the intensity, modulation and configuration, optical system shutter, aperture and focus of the light source array 121 by providing control signals 134 to the power management system 139, the optical imaging system 126, the onboard storage 131, optional Heads-Up display 138 and the onboard video display 128 and according to an alternative embodiment, receive optional remote input from an external, optional computing system 132 discussed below. According to this alternate embodiment, the optional computing system 132 can be a tablet, laptop or a desktop computer onsite or networked from a remote location. The present invention employs on-board and off-board peripherals including the video display 128 (e.g., a touchscreen display), the HUD 138 and optional LED indicators (not shown).

Figure 2:
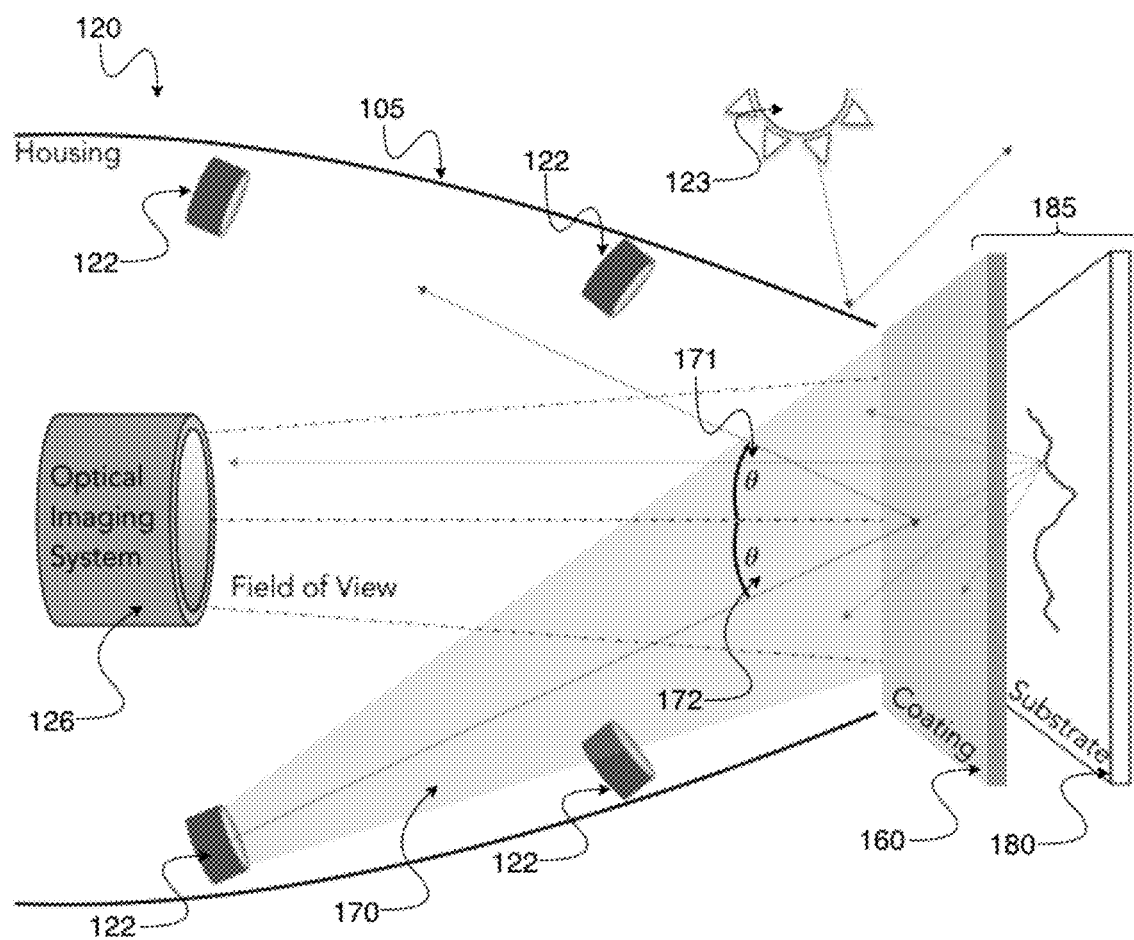
FIG. 2 is a schematic illustrating the detection system and detection method according to one or more embodiments of the present invention.

The optical imaging system 126 is a camera device capable of capturing video and still images of the coating and underlying substrate (160 and 180 as depicted in FIG. 2) can be an any optical imaging system according to an embodiment of the present invention, for example, near-ultraviolet, near-infrared (NIR), shortwave (SWIR) mid-wave (MWIR) and longwave (LWIR) infrared. The optical imaging systems can also include the visible light spectrum of 400 to 700 nanometers. Additional details of the optical imaging system 126 will be discussed below with reference to FIG. 3. According to embodiment, the optical imaging system 126 and the on-board embedded system 130 communicate with each other directly. The on-board embedded system 130 comprises a microcontroller configured to control the optical imaging system 126 via control signals 134, and the light source array 121 along with the other components of the detection device 120. The video data stream 133 from the optical imaging system 126 is processed in real-time and corrected for known spatial intensity variations of the light source array 121; spatial and temporal variations in sensitivity of the optical imaging system 126; and the optical Narcissus effect that occurs when the optical imaging system 126 is an infrared type optical imaging system. In addition, the on-board embedded system 130 is capable of performing edge detection, feature identification and highlighting and false color rendering. As Infrared optical systems are sensitive to the blackbody radiation present in all objects, they will often image their own heat signature in the reflections from flat surfaces oriented perpendicular to the optical axis 145. This self-generated image is known as the optical Narcissus effect and can be significantly prominent in cooled focal plane arrays 141 where the sensor is very cold compared to the surrounding structure, resulting in a dark spot in the center of the image. The on-board embedded system 130 is configured to optionally pulse or otherwise modulate the intensity of the light source array 121 via pulse width modulation (PWM) techniques to provide a lock-in image detection function for improved fidelity and signal-to-noise performance. Upon receiving control signals from the onboard controls 124 the on-board embedded system 130 will employ high precision, low power PWM output signals to drive the light source array 121 with variable signals to modulate the array output intensity with square, sinusoidal or triangular responses. PWM control signals also provide precise control over the overall intensity of the light source array 121, allowing the system to reduce or increase the amount of light directed upon the coated substrate. Optional Lock-in image detection is achieved by modulating the light intensity at a known frequency and subsequently extracting only the components of the captured video data stream 133 that vary at that same expected frequency. The amplitude of the detected modulating signal in the video data stream 133 is the desired image signal whereas all other content is considered background noise and rejected.

According to one or more embodiments, the detection device 120 of the system 100 further includes a detection software module 136 (e.g., an inspection software application) accessible locally via the on-board embedded system 130, and remotely through the optional external computing system 132. The on-board embedded system 130 and optional external computing system 132 are configured to process, display and store information and image data in real-time, record location, and append environmental data from other optional USB or Ethernet-based sensors such as GPS or local geolocation systems, temperature and local relative humidity, automate reporting, maintain a database (not shown) of the information and image data, store detection instructions of the detection software module 136, and communication with external components (e.g., other hardware, servers, and networked inspection tools). That is, the detection software module 136 can grab and use information from external sources and incorporate it into the recorded data (e.g. stored images). The on-board embedded system 130 can also execute the detection software module 136 to display the video data stream in real time, and store inspection data as the still images are captured in addition to performing automated reporting of inspection findings, storing user instructions for reference, monitoring system messages and status thereof and communicating with external, off-board peripherals. The on-board embedded system 130 comprises an onboard storage 131. The onboard storage 131 is a database that can include images of previous inspections and examples of hidden damage data for comparison with new image data obtained by the optical imaging system 126.

The on-board embedded system 130 transmits detection instructions from the detection software module 136 to the components of the detection device 120 as indicated by the arrows shown. Alternatively, instructions of the detection software module 136 can be wirelessly transmitted via a wireless communication network (e.g., Wi-Fi or Bluetooth) from the optional external computing system 132. Other wireless networks such as 802.11, 802.15 and cellular networks can also be applicable.

The video data stream 133 is displayed in real-time via the onboard video display 128 and head-up display (HUD) 138, and allows for real-time image processing.

Further, according to one or more embodiments the wearable head-up display (HUD) 138 is in communication with the on-board embedded system 130 to transmit information to the wearable HUD 138. As mentioned above, the communication can be performed via wireless communication or wired communication.

According to an embodiment, the wearable HUD 138 is an optional component which can be employed to further enhance the detection method by allowing an operator to view what is being seen by the detection device 120, while remaining out of local or line-of-sight contact, and allowing the operator to perform single-hand operation of the detection device 120. In this embodiment, the operator of the detection device 120 can wear the HUD 138 which receives the processed video data stream from the on-board embedded system 130. Further, the HUD 138 can include onboard controls similar to the onboard controls 124 of the detection device 120, to control the detection software module 136, and the detection device 120 itself, to adjust (i.e., increase/decrease) the intensity of the light source array, save images and power up/down, for example. That is, the same control operations performed at the detection device 120 can also be performed at the HUD 138.

The detection device 120 of the system 100 further includes a power management system 139 and a battery 140 (e.g., an onboard replaceable or rechargeable battery). The battery 140 is hot-swappable and can be configured for extended runtimes (e.g., approximately 3 hours when the system 100 is implemented as a handheld device). The status of the battery 140 and the power management system 139 can be monitored and controlled, respectively via the detection software module 136. The detection software module 136 can monitor and display battery and system voltages of the battery 140 and the power management system 139. Alternatively, when implemented within a larger device, an onboard or belt clip type battery can be used for extended runtimes of approximately 4-5+ hours. Additionally, can be fitted with wired power for unlimited use. Thus, the system 100 of the present invention is not limited to any particular runtime, and can be varied as needed.

Upon using the detection device 120, the operator can determine how well the coating transparent light 170 transmitted from the light sources 122 of the light source array 121 is penetrating the coating 160 of the coated substrate 185 (as depicted in FIG. 2, for example). Thicker coatings result in less light returning therefrom, thus in this case, more light sources 122 of the light source array 121 can be implemented for better detection. As mentioned above, the light sources 122 of the light source array 121 can be modulated using pulse width modulation (PWM) techniques to maximize intensity, minimize power requirements and improve fidelity over limitations imposed by inherent spatial variations through the use of lock-in imaging. Additional details regarding operation of the detection system 100 and detection device 120 thereof will be described below with reference to FIGS. 2 through 5.

FIG. 2 is a schematic illustrating the detection device 120 and detection method according to one or more embodiments of the present invention.

As shown in FIG. 2, the detection device 120 further includes a housing 105 that is shaped to block all external light sources 123 from impinging on the area of coated substrate 185 to be inspected, and encases the light source array 121 including the plurality of light sources 122, and the optical imaging system 126 along with the other components of the detection device 120. The housing 105 includes interchangeable forebodies or noses 151 (as depicted in FIG. 4D discussed below) which allow the detection device 120 to be adapted to varying substrate geometries while still blocking all external light sources 123. A spectral bandwidth of the light source array 121 is matched to a transmission spectrum of the coating 160 shown, about the interior of the housing 105 to direct light upon the coated substrate 185 within a field of view of the optical imaging system 126. The light source array 121 including the light sources 122 are configured to avoid direct reflections off the coated substrate 185 into the optical imaging system 126 by ensuring shallow angles of incidence to the coated substrate 185. One or more embodiments of the present invention specifies a mid-wave infrared (MWIR) optical imaging system 126 and light source array 121 for performing the detection method on commercial and military aircraft coatings and substrates. The present invention is not limited to the MWIR ranges (commonly accepted as approximately 3-5 microns) and any other suitable technology can be implemented herein. According to one or more embodiments, the optical imaging system 126 and light source array 121 can be changed to accommodate different transmission properties of coatings 160 or combined with multiple sources to generate images in several bandwidths. For example, the optical imaging system 126 and light source array 121 can be exchanged or combined with components designed for other wavelength ranges such as LWIR (e.g., approximately 8-15 micron wavelength) or SWIR (e.g., approximately 1.4-3 micron wavelength), near infrared (e.g., 0.7-1.4 micron wavelength), or near ultraviolet (e.g., approximately 300-400 nanometer wavelength) such that the detection device 120 can be compatible with a wide range of coatings 160 and the detection device 120 can be implemented within a larger instrument or an instrument with swappable modules configured for different wavelength ranges. Most coatings of interest are intended to be opaque in the visible light spectrum, however extremely narrow transmission bands do exist in the visible spectrum of some coatings, and thus the system described is a viable approach as high-efficiency, narrow band light sources in the visible spectrum are common.

Figure 3:
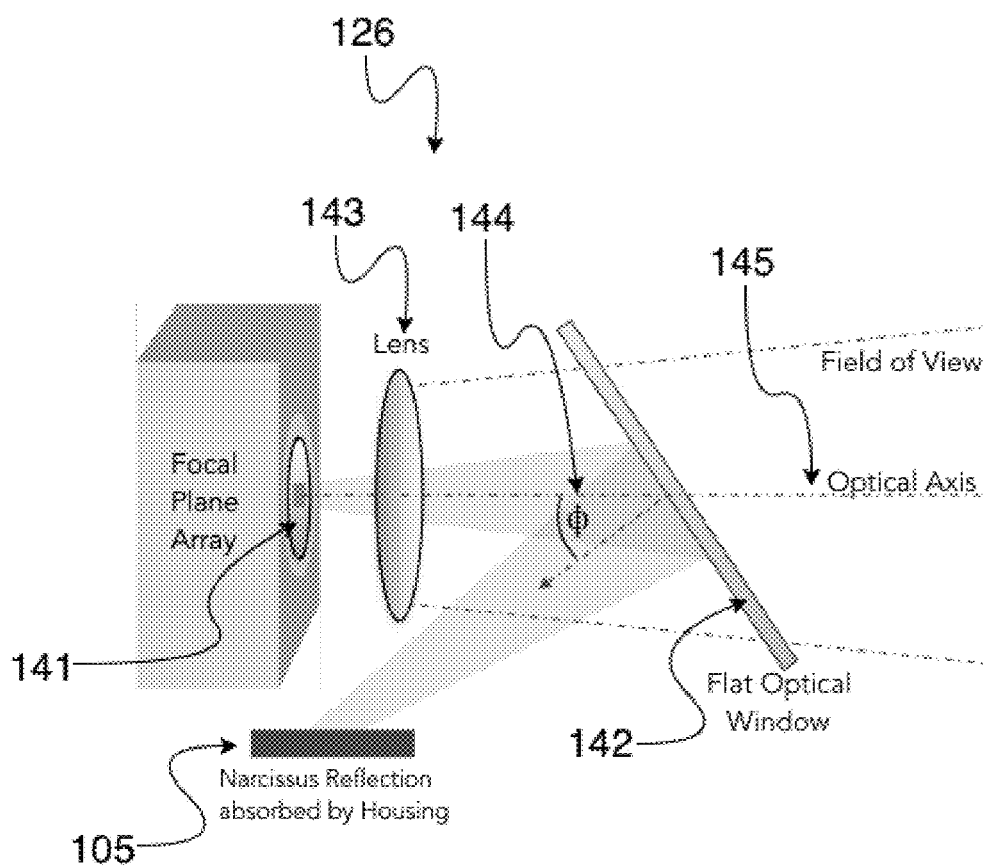
FIG. 3 is a schematic illustrating the detection system and detection method according to one or more alternative embodiments of the present invention.

According to an embodiment of the present invention, the optical imaging system 126 has an integrated heat sink (not shown) and a small fan (not shown) to be used to pull cool air through the housing 105. According to one or more embodiments, the housing 105 is configured to block and eliminate all external light sources 123 to minimize unwanted light interference and ensure a high signal-to-noise ratio in the detected video data stream 133 (as depicted in FIG. 1). The housing 105 is shaped to block the external sources of lights from impinging a section of coated substrate 185 under inspection, within a field of view of the optical imaging system 126 (as depicted in FIG. 3). The housing 105 is constructed such that the front edge which contacts the coated substrate 185 is of a non-marring or rubberized material.

As shown, the light source array 122 is positioned at angle of incidence theta ($\theta$) to cast coating transparent light 170 onto the coated substrate 185 while avoiding direct reflections (at angle of reflection ($\theta$) 171) back into the optical imaging system 126. Light is reflected and scattered from underlying surface of the substrate 180 (e.g., substructure) of the coated substrate 185 and collected by the optical imaging system 126.

According to other embodiments of the present invention, additional spectral filter(s) can be used to decrease the imaging bandwidth depending on the transmission properties of the target coating of the coated substrate 185. That is, if the transmission band of the coating under inspection is narrower than expected and there is too much reflected or absorbed light, the bandwidth of detection can be optionally narrowed by the use of spectral filter(s), thereby improving the signal-to-noise of the image captured by the optical imaging system 126.

According to other embodiments of the present invention, optical polarizer(s) can be employed to decrease the amount of unwanted reflected light or increase the signal-to-noise of scattered light from underlying artifacts. The light source array 121 can minimize power requirements, maximize intensity, and homogenize spatial variations through the use of any one of intensity modulation, a plurality of diffusers, a plurality of polarizers, and curved reflectors.

FIG. 3 is a detailed schematic illustrating the optical imaging system 126 according to one or more embodiments of the present inventions.

As shown in FIG. 3, the optical imaging system 126 comprises a focal plane array 141; an imaging lens 143 and an optional flat optical window 142. The focal plane array 141 can be a cryogenically-cooled or uncooled focal plane array. Sensor technologies in the MWIR include cooled Mercury Cadmium Telluride (MCT) or Indium Antimonide (InSB) or uncooled Vanadium Oxide (VOx) based detectors. The lens 143 is positioned via mechanical or electromechanical methods to receive the reflected and scattered light from the underlying surface 180 (depicted in FIG. 2) and produce an image on the focal plane array 141. According to one embodiment, an original equipment manufacturer (OEM) MWIR camera core is employed as the focal plane array 141 and is matched to the wavelength range a MWIR light source array 122. An infrared focal plane array is often cooled, and thus very cold and will detect a self-generated ghost image of the focal plane array 141 retro-reflected from planar surfaces normal to the optical axis. This appears as a central dark spot in close-up optical images known as the optical Narcissus effect.

According to an embodiment, the flat optical window 142 is a Sapphire optic that reduces the optical Narcissus effect caused by the ghost image of cooled focal plane array 141 retro-reflecting off the coating 160 and substrate 180. The flat optical window 142 is positioned at angle (φ) 144 to direct the self-generated ghost image of the cooled focal plane array 141 away, where it can be safely absorbed by the housing 105. Sapphire is chosen for better transmission to the MWIR wavelengths. The present invention however is not limited to employing a Sapphire window, and any suitable type of flat optical window 142 can be employed. Performance of the flat optical window 142 can be further enhanced through the use of anti-reflection thin film coatings on the window 142. Optionally, filters can be added or integrated into the optical components (i.e., the light sources 122 of the light source array 121, the optical imaging system 126, the focal plane array 141, the flat optical window 142, and the lens 143) of the detection system 100 to further restrict the spectral bandwidth of the optical system and increase performance in narrow transmission spectral bands in various coatings.

FIGS. 4A, 4B, 4C and 4D illustrate various applications of the detection device 120 of the detection system 100 according to one or more embodiments. As shown in FIGS. 4A, 4B, and 4C, the detection system 100 can be implemented via a handheld device with an integrated or removable pistol grip 150, or a camcorder-style hand grip and strap. FIGS. 4A, 4B and 4C depict an embodiment where the detection system 100 is configured with the housing 105, the onboard controls 124, the onboard video display 128, a removable battery 140, a removable pistol-style grip 150. FIG. 4D depicts the interchangeable forebodies or noses 151 that allow the detection device 120 to adapt to non-flat substrates such as interior or exterior corners, leading edges, concave or convex panels as well as structural framing including angle iron, T- and I-beams. while still blocking out all unwanted external light. The interchangeable forebodies 151 include soft, pliable or rubberized materials such as rubber lips, rings, bumpers or a bellows that will conform to an irregular surface with light pressure from the operator. Using the same control structure, detection software module 136 and HUD 138, the detection system 100 can be deployed across a scalable platform of applications. The detection system 100 can be implemented within ground-based autonomous, vehicles (flying or crawling drones), robotic arms, sealed in a water-proof housing to be used in underwater applications, or tripod-mounted as a stand-off device.

According to one embodiment, the system 100 can be implemented as a handheld device 150 which is lightweight, rugged and battery-powered and capable of being operated by a single hand of an operator.

The light source array 121 and optical imaging system 126 are removable from the handheld device 150. The handheld device 150 is held right up to the surface of the coated substrate 185 to perform the detection. The optical imaging system 126 has a usable depth of field of approximately 1 inch and allows curved and irregular surfaces to remain in focus. The handheld device 150 includes interchangeable geometry forebodies 151 and materials that adapt the device 150 to substrates 185 (as depicted in FIG. 2) of various geometries such as interior or exterior corners, leading edges, concave or convex panels as well as structural framing including angle iron, T- and I-beams. so as to optimize the blockage of unwanted external light sources impinging on the inspection regime. If the lens 143 is mounted electromechanically, the focus of the optical imaging system 126 can be optimized by the operator for better performance in off-design geometry applications.

Alternatively, the light source array 121 and optical imaging system 126 can be integrated within a standoff or quad-copter-style gimbal mount for remote operation and inspection.

Figure 5:
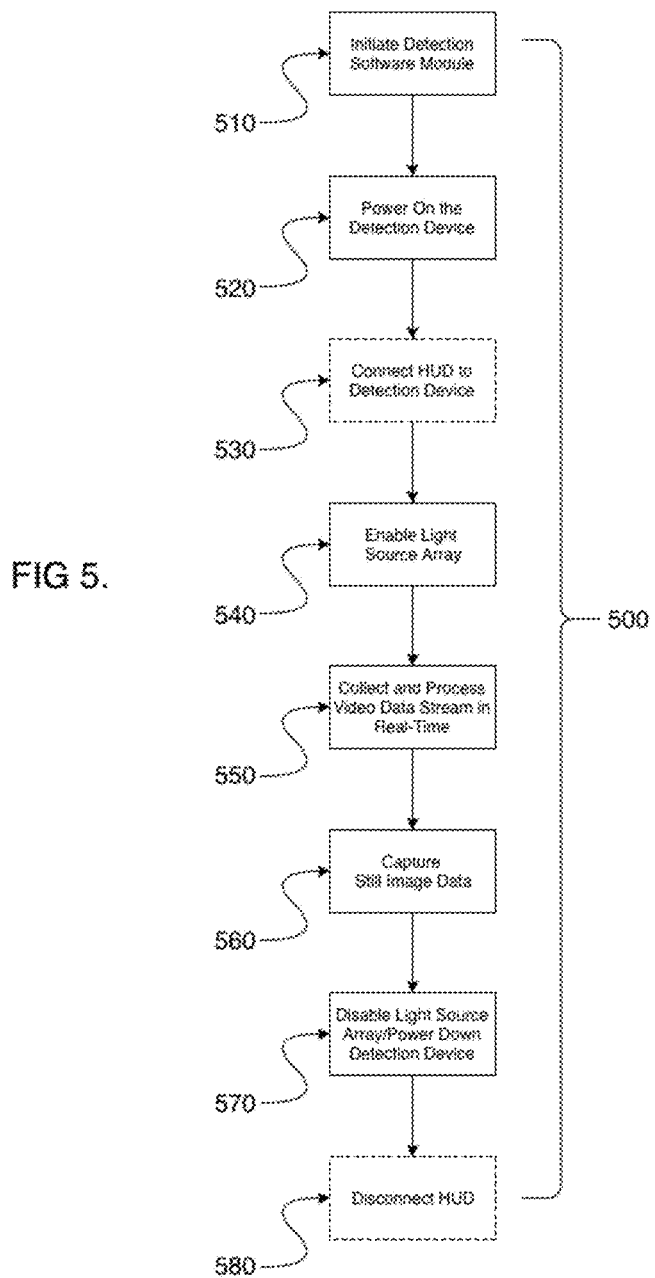
FIG. 5 illustrates a flow diagram showing a detection method of the detection system of FIGS. 1 through 4 that can be implemented according to one or more embodiments.

The detection method 500 of the present invention will now be discussed with reference to FIGS. 1, 2 and 3. All detection system 100 operations described herein can be accomplished via the onboard controls 124 or the optional external computing system 132. As shown in FIG. 5, the detection method 500 includes initiating the detection software module 136 (operation 510), powering up the detection device 120 and the optical imaging system 126 (operation 520). Next, the light source array 121 is enabled (operation 540) and the system 100 collects and processes the video data stream 133 in real-time (operation 550). Then, data is captured using the onboard controls 124 or the remote peripherals (HUD 138 or external computing system 132)

(operation 560). Additionally, descriptive data e.g., location and comments etc. can be added using the above methods, during the process.

Optionally, the method further includes connecting the HUD 138 to the detection device 120, to view the real-time video data stream 133 hands free if desired (operation 530).

According to an embodiment, the information can be prefilled or based on repair and inspection requests, for example, stored within the detection software module 136.

The information obtained can be transmitted in real-time to a facility network or at a later time.

Upon completion of the detection method, the optical imaging system 126 and light source array 121 are disabled (operation 570), the detection device 120 is powered down, and the HUD 138 if employed is disconnected (operation 580).

This written description uses examples to disclose the invention including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A detection system for detecting abnormalities in a coated substrate including a coating and a substrate, the detection system including a detection device comprising:
    a housing configured to block external sources of light from impinging on the coated substrate and comprising:
    a light source array including a plurality of light sources and configured to be arranged to direct light upon the coated substrate;
    an optical imaging system configured to capture a video data stream and still images of the coating and an underlying surface of the substrate including structure features comprising any abnormalities in the coated substrate;
    an on-board embedded system configured to:
        (i) execute a detection software module locally assessible,
        (ii) control the light source array and the optical imaging system,
        (iii) perform real-time processing to correct spatial and temporal variations in intensity of the plurality of light sources of the light source array, and spatial and temporal variations in sensitivity and optical Narcissus effect of the optical imaging system,
        (iv) process, display and store information including detection instructions of the detection software module and image data in real-time, and
        (v) record location at which still images are captured, relative to the coated substrate and append environmental data from external sources; and
    on-board controls connected to the onboard embedded system and configured to adjust parameters of the light source array, by providing control signals to the on-board embedded system to employ pulse width modulation output signals, to drive the light source array with variable signals to modulate an output intensity of the light source array, wherein lock-in image detection is achieved.

2. The detection system of claim 1, wherein the light source array is matched in bandwidth to a spectral transmission band of the coating of the coated substrate.

3. The detection system of claim 2, wherein the light source array is positioned at an angle of incidence to cast coating transparent light onto the coated substrate while avoiding direct reflections at an angle of reflection back into the optical imaging system.

4. The detection system of claim 3, wherein the optical imaging system is matched to a wavelength range of the light source array and configured and positioned to: collect and measure reflected and scattered light from the underlying surface and the coating of the coated substrate.

5. The detection system of claim 1, the detection device further comprising:
    a power management system comprising a battery supplying power for the detection device;
    on-board video display configured to display the video data stream in real-time; and
    the on-board controls further configured provide control signals to the the power management system, the optical imaging system and the on-board video display.

6. The detection system of claim 5, wherein the parameters comprising at least one of intensity, modulation and configuration, optical system shutter, aperture, and focus of the light source array.

7. The detection system of claim 5, wherein the on-board embedded system further comprises an onboard storage configured to store images of previous inspections including hidden damage data for comparison with new image data to be obtained by the optical imaging system.

8. The detection system of claim 5, wherein the on-board embedded system is further configured to transmit detection instructions from the detection software module to components of the detection device.

9. The detection system of claim 8, wherein the optical imaging system comprises:
    a focal plane array;
    an imaging lens positioned to receive the light reflected and scattered from the underlying surface and to produce an image on the focal plane array; and
    an flat optical window being a sapphire optic and configured to reduce the optical narcissus effect caused by a ghost image of the focal plane array when cooled, which is retro-reflected off the coating and the underlying surface of the substrate, and wherein the flat optical window is positioned at an angle to direct the ghost image away so it can be absorbed by the housing.

10. The detection system of claim 9, wherein the imaging lens is compatible with mid-wave infrared (MWIR) light and configured to create an image of the coated substrate on the focal plane array.

11. The detection system of claim 9, wherein the housing is shaped to block the external sources of light from impinging on the coated substrate, within a field of view of the optical imaging system.

12. The detection system of claim 9, wherein the detection device is a handheld device with an integrated grip for single hand operation and configured to be held up to the surface of the coated substrate to perform detection operation.

13. The detection system of claim 11, wherein the housing further comprises interchangeable forebodies configured to adapt to non-flat substrates while blocking out the light from external sources.

14. The detection system of claim 1, further comprising a wearable heads-up display in communication with the onboard embedded system and configured to view the video data stream and still images, in real-time.

15. The detection system of claim 5, further comprising an external computing system in communication with the on-board embedded system and configured to perform same operations as the on-board controls and mirror a display of the on-board video display remotely and in real-time.

16. The detection system of claim 15, wherein the external computing system is a tablet, laptop or desktop computer in wired or wireless communication with the on-board embedded system.

17. A detection method performed by a detection system having a detection device including an on-board embedded system and on-board controls, comprising:
  initiating, via the on-board embedded system, a detection software module locally assessible;
  powering on the detection device including an optical imaging system;
  enabling a light source array and adjusting, via the on-board controls, parameters of the light source array, by providing control signals to the on-board embedded system;
  upon receiving the control signals, employing, via the on-board embedded system, pulse width modulation output signals, to drive the light source array with variable signals to modulate an output intensity of the light source array, wherein lock-in image detection is achieved, thereby collecting and processing video data stream captured via the optical imaging system in real-time to reveal an image of structure features including any abnormalities in the substrate;
  capturing still images;
  processing, displaying and storing information including detection instructions of the detection software module and image data in real-time;
  recording location at which still images are captured, relative to the coated substrate and append environmental data from external sources; and
  disabling the light source array and powering down the detection device.

18. The detection method of claim 17, further comprising:
  connecting a heads-up display to the detection device; and viewing the video data stream in real time; and
  disconnecting the heads-up display upon disabling the light source array and powering down of the detection device.

* * * * *